(12) United States Patent
Stephens

(10) Patent No.: US 10,005,994 B2
(45) Date of Patent: Jun. 26, 2018

(54) SYSTEMS AND METHODS FOR ANAEROBIC DIGESTION AND COLLECTION OF PRODUCTS

(75) Inventor: James Stephens, Missoula, MT (US)

(73) Assignee: Blue Marble Energy Corporation, Missoula, MT (US)

(*) Notice: Subject to any disclaimer, the term of this patent is extended or adjusted under 35 U.S.C. 154(b) by 1659 days.

(21) Appl. No.: 14/009,308

(22) PCT Filed: Oct. 21, 2009

(86) PCT No.: PCT/US2009/005769
§ 371 (c)(1),
(2), (4) Date: Feb. 11, 2014

(87) PCT Pub. No.: WO2010/047815
PCT Pub. Date: Apr. 29, 2010

(65) Prior Publication Data
US 2014/0154754 A1    Jun. 5, 2014

Related U.S. Application Data

(60) Provisional application No. 61/107,279, filed on Oct. 21, 2008.

(51) Int. Cl.
| C12M 1/107 | (2006.01) |
| C12M 1/00 | (2006.01) |
| C12P 3/00 | (2006.01) |
| C12P 5/02 | (2006.01) |
| C12P 7/40 | (2006.01) |
| C12P 7/64 | (2006.01) |

(52) U.S. Cl.
CPC ............ *C12M 21/04* (2013.01); *C12M 21/12* (2013.01); *C12M 23/58* (2013.01); *C12M 43/06* (2013.01); *C12M 43/08* (2013.01); *C12P 3/00* (2013.01); *C12P 5/023* (2013.01); *C12P 7/40* (2013.01); *C12P 7/6409* (2013.01); Y02E 50/343 (2013.01)

(58) Field of Classification Search
CPC .................................................. C12M 23/58
See application file for complete search history.

(56) References Cited

U.S. PATENT DOCUMENTS

| 4,022,665 | A | | 5/1977 | Ghosh et al. | |
| 4,372,856 | A | * | 2/1983 | Morrison | C02F 3/28 126/572 |
| 4,696,746 | A | * | 9/1987 | Ghosh | C02F 3/286 210/218 |
| 4,869,819 | A | * | 9/1989 | Thiele | B01J 41/046 210/195.1 |
| 6,299,774 | B1 | * | 10/2001 | Ainsworth | C02F 3/28 210/178 |
| 6,921,485 | B2 | * | 7/2005 | Kilian | C02F 3/2853 210/195.3 |
| 7,811,455 | B2 | | 10/2010 | Burke | |
| 2002/0162794 | A1 | | 11/2002 | Tock | |
| 2005/0139546 | A1 | * | 6/2005 | Burke | C02F 1/20 210/603 |
| 2008/0187975 | A1 | * | 8/2008 | Kohn | C01B 3/501 435/167 |
| 2009/0017513 | A1 | | 1/2009 | Bell | |

FOREIGN PATENT DOCUMENTS

| EP | 0159054 A1 | 10/1985 |
| EP | 1403222 A1 | 3/2004 |
| WO | WO-2006107696 A2 | 10/2006 |
| WO | WO 2006/119052 A2 | 11/2006 |
| WO | WO 2008/076423 A1 | 6/2008 |
| WO | WO-2008066546 A1 | 6/2008 |
| WO | WO 2010/046913 A2 | 4/2010 |
| WO | WO 2010/046914 A1 | 4/2010 |

OTHER PUBLICATIONS

Blonskaja, et al. Use of two-stage anaerobic treatment for distillery waste. Advance in Environmental Research. May 1, 2003; 7(3):671-678.
Bouallagui, et al. Bioreactor performance in anaerobic digestion of fruit and vegetable wastes. Process Biochemistry. 2005; 40:989-995.
Chynoweth, et al. Renewable methane from anaerobic digestion of biomass. Renewable energy. 2001; 22:1-8.
European search report and opinion dated Jan. 8, 2014 for EP Application No. 09822331.6.
Fang, et al. Performance and sluge characteristics of UASB process treating propionate-rich wastewater. Water Research. Mar. 1, 1995; 29(3):895-898.
Gijzen, et al. High-rate two-phase process for the anaerobic degradation of cellulose, employing rumen microorganisms for an efficient acidogenesis. Biotechnology and Bioengineering. Apr. 5,1988; 31(5):418-425.
International search report and written opinion dated May 26, 2010 for PCT/US2009/005769.
Uludag-Demirer, et al. Ammonia removal from anaerobically digested dairy manure by struvite precipitation. Process Biochemistry. Dec. 1, 2005; 40(12):3667-3674.
Wang, et al. A bench scale of fermentative hydrigen and methane production from food waste in integrated two-stage process. International Journal of Hydrogen Energy. Jan. 1, 2009; 34(1):245-254.

(Continued)

*Primary Examiner* — Renee Claytor
*Assistant Examiner* — Susan E. Fernandez
(74) *Attorney, Agent, or Firm* — Lee & Hayes, PLLC

(57) ABSTRACT

Described herein are methods and systems that can provide independent energy generation as well as systems for the generation of other useful products, such as chemicals. In addition, the systems and methods can provide ways of harnessing the potential of biomass feedstock to generate of multitude of products including green crude, biogas, electricity, heat, fatty acids, biodiesel, ammonia, and chemical products. In many cases, the systems and methods herein utilize anaerobic microorganisms, including aquatic and ruminant organisms, to digest material and create products.

25 Claims, 6 Drawing Sheets

(56) References Cited

OTHER PUBLICATIONS

Wang, et al. Effect of acidification percentage and volatile organic acids on the anaerobic biological process in simulated landfill bioreactors. Process Biochemistry. Jul. 1, 2006; 41(7):1677-1681.
Leschine. Cellulose degradation in anaerobic environments. Annual review of microbiology, 1995, vol. 49, pp. 399-426.

* cited by examiner

Primary Tank: VFA / Cellulostic Fermentation Tank

Primary Fermentation Tank: Cellulostic Fermentation (Cellulose → Cellubiose → Glucose → Volatile Fatty Acids), Ammonification (Protein (NH2 groups) → NH3 (NH4, anoxic)), Desulfurylation (Protein (Organic S) → H2S)

Microbial Species: *Fibrobacter succinogenes, Butyrivibrio fibrisolvens, Ruminococcus albus, Clostridium locheadii, Bacteroides ruminicola, Ruminobacter amylophilus, Selenomonas ruminantium, Succinomonas amylolytica,Streptococcus bovis* (unwanted microorganism, leads to acidification of the primary fermentation tank) , *Selenomonas lactilytica, Megasphaera elsdenii, Schwartzia sunniovorans, Lachnospira mulitparus, Neocalimastix* (fungus, ferments non-cellulose starches)

Primary Fermentation Tank Products: Biogas (H2, CO2, H2S, CH4 (residual)), H2O, Acetate -, Propionate -, Butyrate-, NH3 / NH4+

Secondary Tank: Biogas Production / Anaerobic Digestion / Methane Generation Tank Secondary Fermentation Tank: Methanogenesis (Fatty Acids, CO2, H2 → CH4), Ammonification (Protein (NH2 groups) → NH3 (NH4, anoxic)), Desulfurylation (Protein (Organic S) → H2S)

Microbial Species: *Methanobrevibacter ruminantium* (CO2 + H2 → CH4), *Methanomicrobium mobile* (CO2 + H2 →CH4)
Secondary Microbial Species: Syntrophomonas wolfei (fatty acids → acetate, CO2, H2)), Other syntrophic methanogens
Secondary Fermentation Tank Products: Biogas (CH4, H2S, CO2), NH3/NH4+, Biomass Slurry Secondary Fermentation: Biogas (CH4, H2S, CO2, H2O), Biomass Slurry, NH3/NH4+

Figure 1

| 1 KG Sample Set | | | | | | | | | | |
|---|---|---|---|---|---|---|---|---|---|---|
| Feedstock | Range | acetate | propionate | butyrate | CO2 | methane | water | formate | ammonia | total |
| Ulva Lactica | Low | 170.67 | 64.78 | 57.78 | 216.15 | 75.38 | 45.02 | 22.59 | 31.18 | 683.56 |
| | Medium | 187.55 | 71.19 | 63.50 | 237.53 | 82.84 | 49.47 | 24.82 | 34.27 | 751.16 |
| | High | 202.56 | 76.89 | 68.58 | 256.53 | 89.46 | 53.43 | 26.81 | 37.01 | 811.26 |
| Puget Sound Wild Algae Mix | Low | 136.64 | 51.87 | 46.26 | 210.01 | 102.74 | 47.39 | 31.62 | 36.41 | 662.94 |
| | Medium | 160.76 | 61.02 | 54.43 | 247.07 | 120.87 | 55.75 | 37.20 | 42.84 | 779.93 |
| | High | 178.44 | 67.73 | 60.41 | 274.25 | 134.17 | 61.88 | 41.29 | 47.55 | 865.72 |
| Waste Water Microalgae | Low | 143.08 | 54.31 | 48.44 | 219.89 | 107.57 | 49.62 | 33.10 | 38.12 | 694.14 |
| | Medium | 160.76 | 61.02 | 54.43 | 247.07 | 120.87 | 55.75 | 37.20 | 42.84 | 779.93 |
| | High | 165.58 | 62.85 | 56.06 | 254.48 | 124.50 | 57.42 | 38.31 | 44.12 | 803.33 |
| Milfoil / Duckweed | Low | 143.08 | 54.31 | 48.44 | 219.89 | 107.57 | 49.62 | 33.10 | 38.12 | 694.14 |
| | Medium | 160.76 | 61.02 | 54.43 | 247.07 | 120.87 | 55.75 | 37.20 | 42.84 | 779.93 |
| | High | 181.66 | 68.95 | 61.50 | 279.19 | 136.58 | 63.00 | 42.03 | 48.40 | 881.32 |
| Spent Grain | Low | 107.64 | 40.86 | 36.44 | 201.46 | 141.01 | 50.01 | 42.24 | 39.84 | 659.51 |
| | Medium | 115.75 | 43.94 | 39.19 | 216.63 | 151.63 | 53.77 | 45.42 | 42.84 | 709.15 |
| | High | 131.95 | 50.09 | 44.67 | 246.95 | 172.85 | 61.30 | 51.78 | 48.83 | 808.43 |
| Dried Distillers Grain | Low | 88.46 | 33.58 | 29.95 | 188.49 | 191.57 | 52.40 | 54.02 | 39.84 | 678.30 |
| | Medium | 95.12 | 36.10 | 32.20 | 202.67 | 205.99 | 56.35 | 58.09 | 42.84 | 729.36 |
| | High | 103.68 | 39.35 | 35.10 | 220.91 | 224.53 | 61.42 | 63.32 | 46.69 | 795.00 |
| Yard Waste | Low | 190.98 | 72.49 | 64.66 | 170.26 | 46.05 | 32.18 | 8.74 | 12.72 | 598.08 |
| | Medium | 235.78 | 89.50 | 79.83 | 210.20 | 56.85 | 39.73 | 10.79 | 15.71 | 738.37 |
| | High | 249.93 | 94.87 | 84.62 | 222.81 | 60.26 | 42.12 | 11.43 | 16.65 | 782.67 |
| Food Waste | Low | 139.99 | 53.14 | 47.40 | 138.49 | 251.51 | 45.25 | 56.06 | 13.56 | 745.41 |
| | Medium | 147.36 | 55.94 | 49.89 | 145.78 | 264.75 | 47.63 | 59.01 | 14.28 | 784.64 |
| | High | 165.05 | 62.65 | 55.88 | 163.28 | 296.52 | 53.35 | 66.09 | 15.99 | 878.80 |

Figure 6

SYSTEMS AND METHODS FOR ANAEROBIC DIGESTION AND COLLECTION OF PRODUCTS

CROSS-REFERENCE

This application is a US. National Phase Application under 35 U.S.C. § 371 of International Application No. PCT/US2009/005769, filed Oct. 21, 2009, which claims the benefit of U.S. Provisional Application No. 61/107,279, filed Oct. 21, 2008, the entire contents of each of which are hereby incorporated by reference in their entirety.

BACKGROUND OF THE INVENTION

Anaerobic digestion has been used in local communities to generate natural gas and other valuable bio-chemical streams. Anaerobic digestion is a series of processes in which microorganisms break down biodegradable material in the absence of oxygen. It has widely been used to treat wastewater sludges and organic wastes, such as sewage sludge and manure. Anaerobic digestion provides a renewable energy source because the process produces a methane and carbon dioxide rich biogas suitable for energy production.

Local anaerobic digestion systems have offered the cheap, low-cost energy for cooking performing daily tasks and have been recognized by the United Nations Development Program as a decentralized source of energy. Pressure from environmentally-related legislation on solid waste disposal methods in developed countries, such as the United States, has increased the application of anaerobic digestion as a process for reducing waste volumes and generating useful by-products. Anaerobic digestion has typically been used to process separated fractions of municipal wastes.

New technologies are emerging to convert cellulose-containing biomass into useful products, such as electricity, energy, and fuel. Much research has focused on the utilization of algae because of its ability to grow quickly and in many different conditions. In addition, algae can comprise high amounts of lipids and hydrocarbons as compared to other biomass. There is a need in the art to convert biomass, including aquatic biomass, into useful products without requiring high costs or energy demands.

SUMMARY OF THE INVENTION

In an aspect, a bioreactor system is disclosed herein that comprises: a first module comprising a first plurality of anaerobic bacteria; and a second module comprising a second plurality of anaerobic bacteria; wherein an output of the first module is in communication with an input of the second module, and wherein the first plurality of anaerobic bacteria comprises a different mixture of anaerobic bacteria than the second plurality of anaerobic bacteria, and wherein the bioreactor system is configured to remove of volatile fatty acids from the first module and is configured to remove ammonia from the second module in order to maintain the pH of the bioreactor system between 5.9 and 8.5. In some instances, a majority of the first plurality of anaerobic bacteria is acidogenic bacteria, and wherein a majority of the second plurality of anaerobic bacteria is acetogenic bacteria. In some instances, a majority of the first plurality of anaerobic bacteria is acidogenic bacteria, and wherein a majority of the second plurality of anaerobic bacteria is methanogenic bacteria. In some instances, without the removal of volatile fatty acids, the pH of the system is not maintained 5.9 and 8.5. In some instances, the first and second pluralities of anaerobic bacteria each comprise aquatic anaerobic bacteria and ruminant anaerobic bacteria.

In some instances, a majority of the first plurality of anaerobic bacteria is ruminant anaerobic bacteria, and wherein a majority of the second plurality of anaerobic bacteria is aquatic anaerobic bacteria. In some instances, the first plurality of anaerobic bacteria comprises the ruminant anaerobic bacteria in a volume:volume ratio of about 100:1 to 1500:1 of the aquatic anaerobic bacteria, and wherein the second plurality of anaerobic bacteria comprises the aquatic anaerobic bacteria in a volume:volume ratio of about 100:1 to 1500:1 of the ruminant anaerobic bacteria. In some instances, the ruminant anaerobic bacteria is selected from the group consisting of the following: *Fibrobacter succinogenes, Butyrivibrio fibrisolvens, Ruminococcus albus, Clostridium locheadii, Bacteroides ruminicola, Ruminobacter amylophilus, Selenomonas ruminantium, Succinomonas amylolytica, Streptococcus bovis, Selenomonas lactilytica, Megasphaera elsdenii, Schwartzia sunniovorans, Lachnospira mulitparus, Neocalimastix*, and a combination thereof. In some instances, the aquatic anaerobic bacteria is selected from the group consisting of the following: *Methanobrevibacter ruminantium, Methanomicrobium mobile, Syntrophomonas wolfei*, and a combination thereof.

In some instances, the system is a batch system. In some instances, the system is a continuous system. In some instances, the first module comprises an input configured to receive a feedstock, wherein the feedstock comprises solid cellulosic biomass. In some instances, the first module comprises an output configured to collect volatile fatty acids from the bioreactor system. In some instances, the second module comprises an output configured to collect ammonia from the bioreactor system. In some instances, the second module comprises an output configured to collect methane from the bioreactor system.

In an aspect, a bioreactor system is disclosed herein for converting cellulose-containing feedstock into products, wherein the system comprises: a first module comprising an input, more than one output, a first plurality of anaerobic microbes, and the cellulose-containing feedstock, wherein first plurality of anaerobic microbes digest the cellulose-containing feedstock to generate an organic acid product and a partially-digested feedstock; a first separator in communication with one of the outputs of the first vessel, wherein the first separator obtains the organic acid product; a second module comprising an input, more than one output, and a second plurality of anaerobic microbes, wherein the input receives the partially-digested feedstock, and wherein the second plurality of anaerobic microbes digest the partially-digested feedstock to generate a methane product and an ammonia product; and a second separator in fluid communication with one of the outputs of the second module, wherein the second separator obtains the ammonia product. In some instances, the first plurality of anaerobic microbes comprises ruminant anaerobic bacteria. In some instances, the second plurality of anaerobic microbes comprises aquatic anaerobic bacteria. In some instances, the first plurality of anaerobic microbes comprises the ruminant anaerobic bacteria in a volume:volume ratio of about 100:1 to 1500:1 of the aquatic anaerobic bacteria, and wherein the second plurality of anaerobic microbes comprises the aquatic anaerobic bacteria in a volume:volume ratio of about 100:1 to 1500:1 of the ruminant anaerobic bacteria.

In an aspect, a bioreactor comprises: a first plurality of bacteria, wherein the first plurality of bacteria comprises aquatic anaerobic bacteria; and a second plurality of bacteria, wherein the second plurality of bacteria comprises ruminant anaerobic bacteria. In some instances, the bioreactor comprises at least two modules. In some instances, the bioreactor is a continuous system.

In some instances, the first plurality of bacteria is present in a volume:volume ratio of about 1:1 to the second plurality of bacteria. In some instances, the first plurality of bacteria is present in a volume:volume ratio of about 1:100 to 1:1500 to the second plurality of bacteria in a first module of the two modules and the second plurality of bacteria is present in a volume:volume ratio of about 1:100 to 1:1500 to the first plurality of bacteria in a second module of the two modules.

In some instances, the bioreactor comprises an input for cellulose-containing feedstock and at least one output, wherein the output of the bioreactor consists of at least one of the following: ammonia, volatile fatty acids, and methane. In some instances, the output of the bioreactor provides the methane to a turbine configured to deliver electricity.

In an aspect, a method of collecting products from cellulose-containing feedstock herein comprises: delivering the cellulose-containing feedstock to a bioreactor, wherein the bioreactor comprises a plurality of anaerobic bacteria; converting the cellulose-containing feedstock to usable products within the bioreactor, wherein the usable products include at least one of the following: ammonia, volatile fatty acids, and methane; and collecting the usable products from the bioreactor, wherein 59% or greater of the cellulose-containing feedstock is converted to the usable products.

In some instances, the plurality of anaerobic bacteria comprises: a first plurality of bacteria, wherein the first plurality of bacteria comprises aquatic anaerobic bacteria; and a second plurality of bacteria, wherein the second plurality of bacteria comprises ruminant anaerobic bacteria. In some instances, the plurality of anaerobic bacteria comprises: a first plurality of bacteria, wherein the first plurality of bacteria comprises acetogenic bacteria; and a second plurality of bacteria, wherein the second plurality of bacteria comprises acidogenic bacteria, wherein the acidogenic bacteria and acetogenic bacteria are present in the bioreactor at a ratio such to maintain the pH of the bioreactor between 5.9-8.5. In some instances, the first plurality of bacteria is present in a volume:volume ratio of about 1:100 to 1:1500 to the second plurality of bacteria in a first module of the bioreactor and the second plurality of bacteria is present in a volume:volume ratio of about 1:100 to 1:1500 to the first plurality of bacteria in a second module of the bioreactor.

In some instances, a method herein further comprises converting the usable products to electricity. In some instances, a method herein further comprises converting the usable products to biofuel.

In an aspect, a method comprises: combining a plurality of aquatic microorganisms with a plurality of microorganisms from a ruminant stomach in a vessel; maintaining a pH in the vessel between 5.9-8.5; and maintaining a pressure in the vessel between 0.5-10 atm. In some instances, the maintaining the pH in the vessel is carried out by removing ammonia when the pH is greater than 8.5, and removing volatile fatty acids when the pH is below 5.9.

In an aspect, a method of converting cellulose-containing feedstock into products herein comprises: anaerobically digesting or breaking down the cellulose-containing feedstock in a first anaerobic digestion module to produce an organic acid product and a partially-digested feedstock; separating the organic acid product from the partially-digested feedstock; transferring the partially-digested feedstock to a second anaerobic digestion module; anaerobically digesting or breaking down the partially-digested feedstock in the second anaerobic digestion module to produce an ammonia product and a methane product; and removing the ammonia product and the methane product from the second anaerobic digestion module.

INCORPORATION BY REFERENCE

All publications, patents, and patent applications mentioned in this specification are herein incorporated by reference to the same extent as if each individual publication, patent, or patent application was specifically and individually indicated to be incorporated by reference.

BRIEF DESCRIPTION OF THE DRAWINGS

Many novel features of the invention are set forth with particularity in the appended claims. A better understanding of the features and advantages of the invention will be obtained by reference to the following detailed description that sets forth illustrative embodiments, in which many principles of the invention are utilized, and the accompanying drawings of which:

FIG. 1 illustrates an exemplary embodiment of a system of the invention comprising a primary and a secondary fermentation tank, where the primary fermentation can comprise ruminant microbial species and the secondary fermentation tank can comprise methanogens.

FIG. 6 illustrates the conversion of the particular feedstocks in this exemplary system into selected products.

DETAILED DESCRIPTION OF THE INVENTION

Figure 2:
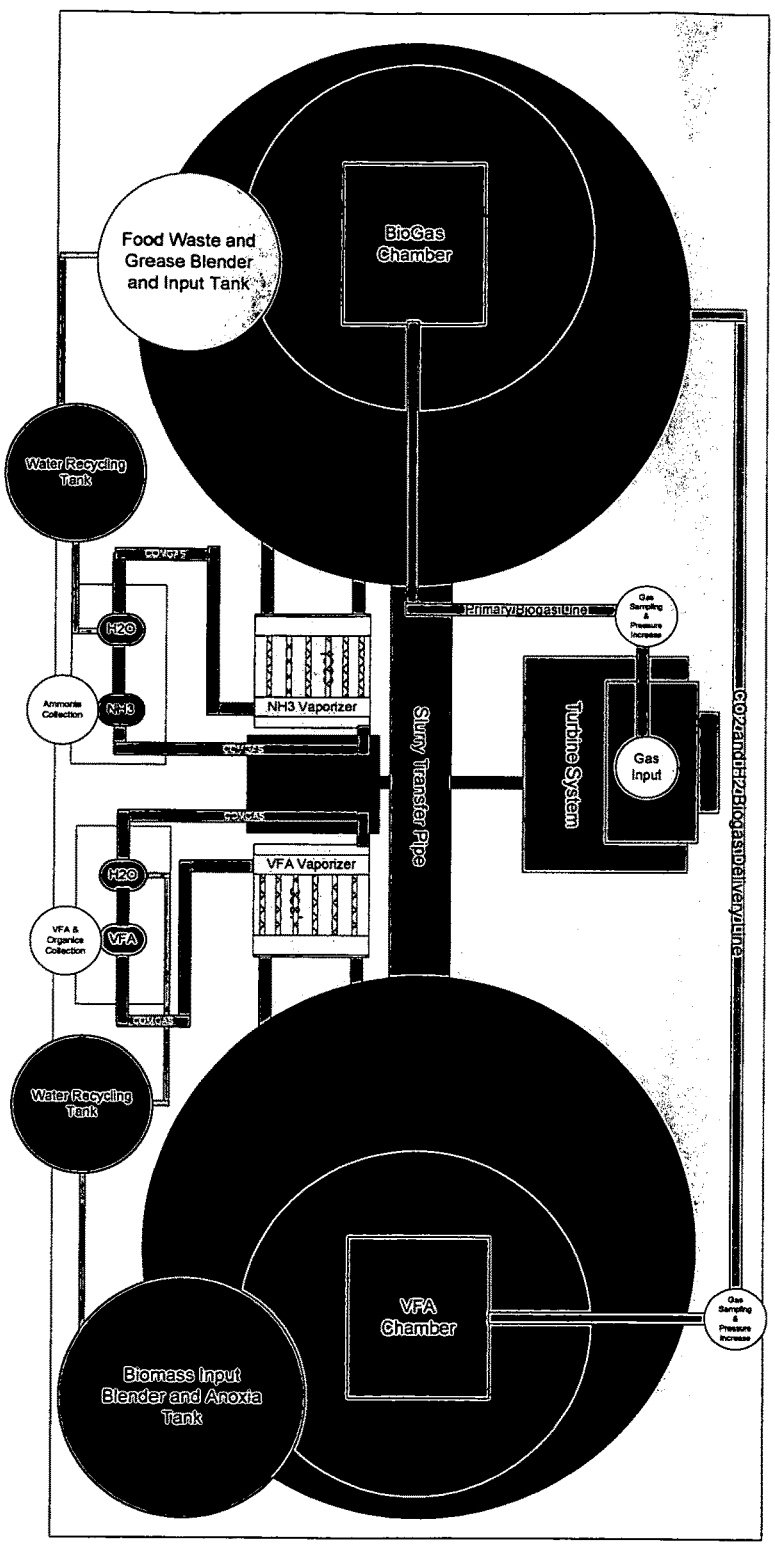
FIG. 2 demonstrates an exemplary system of the invention comprising two fermentation tanks, and at least to separators for obtaining products from the fermentation tanks.

Described herein are methods and systems that provide a combination of independent energy generation as well as systems for the generation of other useful products, such as chemicals. In addition, the systems and methods can provide ways of harnessing the potential of biomass feedstock to generate a multitude of products including green crude, biogas, electricity, heat, fatty acids, biodiesel, ammonia, and chemical products.

Anaerobic digestion is a series of processes in which microorganisms break down biodegradable material in the absence of oxygen. Anaerobic digestion can be used as a renewable energy source because the process produces many products including biogas.

Anaerobic digestion involves microbes that are capable of breaking down materials without the presence of oxygen. The microbiology and biochemistry of anaerobic digestion involves several distinct pools of microbes, each performing specific task of the overall degradation. Typical anaerobic degradation process occurs in four main steps and involves at least three bacterial groups. The anaerobic digestion process of materials by microbes begins with hydrolysis of the input materials in order to break down insoluble organic polymers such as carbohydrates. Acidogenic microbes then convert the sugars and amino acids into carbon dioxide, hydrogen, ammonia, and organic acids. Acetogenic microbes then convert these resulting organic acids into acetic acid, along with additional ammonia, hydrogen, and carbon dioxide. Methanogenic microbes are able to convert the resulting products to methane and carbon dioxide.

Many feedstocks can be processed through anaerobic digestion. In many embodiments, feedstocks comprise any cellulose containing material such as biodegradable waste materials. Organic material can be made into biogas. Heteroatoms such as nitrogen and sulfur that may be present in the feedstock can be converted to ammonia and hydrogen sulfide, respectively. As an example, a feedstock can comprise any animal or plant derived material that contains one or more components that can be converted, bioconverted or biodegraded into a useful material by an anaerobic digestion system of the invention. Animal tissue, biomass, fish tissue or parts, plant parts, fruits, vegetables, plant processing waste, animal processing waste, animal manure or urine, mammalian manure or urine solids isolated from fermentation cultures, and combinations thereof can be biodegraded in an anaerobic digestion system herein. Particular examples of feedstock include bovine, poultry, equine or porcine manure or urine, wood shavings or chips, slops, mostos, shredded paper, cotton burrs, grain, chaff, seed shells, hay, alfalfa, grass, leaves, sea shells, seed pods, corn shucks, weeds, aquatic plants, algae and fungus and combinations thereof. Other examples of feedstocks for the primary or secondary fermentation tanks of a system of the invention include, but are not limited to, wastewater, manure or other waste streams from a food processing plant, or a cheese processing plant. Anaerobic digestion systems can also be fed with specially grown energy crops such as silage for dedicated biogas production. In another example, algae or other aquatic photosynthetic organism can be processed through anaerobic digestion. In some instances, a biomass feedstock herein comprises solid cellulosic biomass. In some instances, the biomass feedstock can comprise solid and liquid biomass. In some instances, the biomass feedstock comprises a majority of solid biomass.

Utilizing anaerobic digestion technologies can help to reduce the emission of greenhouse gases in a number of ways including, for example without limitation, replacement of fossil fuels, reducing methane emission from landfills, displacing industrially-produced chemical fertilizers, reducing vehicle movements, and reducing electrical grid transportation losses.

There are a number of microbes that are involved in the process of anaerobic digestion including acetic acid-forming microbes (acetogens) and methane-forming microbes (methanogens). These microbes feed upon the feedstock, which undergoes a number of different processes converting it to intermediate molecules such as sugars, hydrogen, acetic acid, and biogas.

Different species of microbes are able to survive at different temperature ranges. Microbes living optimally at temperatures between 20-45° C. are called mesophiles or mesophilic microbes. Some of the microbes can survive at higher temperatures, for example 45-80° C. and are called thermophiles or thermophilic microbes. Methanogens can be from the primitive group of archaea that includes species that can grow in the hostile conditions of hydrothermal vents. These species are more resistant to heat and can therefore operate at thermophilic temperatures.

In an embodiment, methods are performed at mesophilic temperatures. There are a greater number of species of mesophiles than thermophiles. These microbes are also more tolerant to changes environmental conditions than thermophiles. Mesophilic systems are sometimes considered to be more stable than thermophilic digestion systems.

The anaerobic microbe used in an anaerobic digestion system herein can also be any anaerobic bacterium, fungus, mold or alga, or progeny thereof, which is capable of converting the feedstock to a useful material. In an embodiment, microbes have been genetically altered or engineered to convert a feedstock to a useful material. Some anaerobic microbes can convert a cellulose-containing feedstock into a variety of products including without limitation: methane, a nitrogen rich fertilizer, charcoal, humus, biogas, volatile fatty acids (UFAs), and an insecticidal slurry.

As mentioned above, thermophilic digestion systems are considered to be less stable, however the increased temperatures facilitate faster reaction rates and hence faster gas yields. Operation at higher temperatures facilitates greater sterilization of the end digestate. In an embodiment, one or more tanks of the system is a thermophilic tank. In another embodiment, one or more tanks is a mesophilic tank.

Generally, a mesophile prefers operating temperatures in the range of about 60°-120° F. or ambient temperature and a thermophile prefers operating temperatures in the range of about 120°-160° F. Examples of an anaerobic microbe which is useful in an anaerobic digestion system of the invention include but are not limited to: yeast, a methanogenic bacterium, methanobacterium, acetobacterium, acetogenic bacterium, liquefaction bacterium, *Clostridium* spp., *Bacillus* spp., *Escherichia* spp., *Staphylococcus* spp., *Methanobacter* spp., *Methanobacter* (*Mb.*) *omlianskii, Mb. formicicum, Mb. soehngenii, Mb. thermoautrophicum, Mb. ruminatium, Mb. mobile, Mb. methanica, Methanococcus* (*Mc.*) *mazei, Mc. vannielii, Mb. suboxydans, Mb. propionicum, Methanosarcina* (*Ms.*) *bovekeri, Ms. mazei, Ms. methanica, Ms. alcaliphilum, Ms. acetivorans, Ms. thermophilia, Ms. barkeri, Ms. vacuolata, Propionibacterium acidi-propionici, Saccharomyces cerevisae, S. ellipsoideus, Clostridium propionicum, Clostridium saccharoacetoper-butylicum,* and *Clostridium butyricum*. Other examples of anaerobic microbes are those found in a ruminant stomach. Other microbes and/or enzymatic catalysts can be added to the anaerobic digestion system to facilitate breakdown of the feedstock into components which are usable by the anaerobic microbe as either nutrients or starting materials for useful materials made by the anaerobic microbe. Such other microbes and/or enzymes include, for example, amylases, proteases, cellulases, hydrolases, lipid hydrolyzing enzymes, lysozymes, phosphatases, esterases, amidases, and lipases.

In an anaerobic system there is an absence of gaseous oxygen. In an embodiment, gaseous oxygen is prevented from entering the system through physical containment in sealed tanks. Anaerobes can access oxygen from sources other than the surrounding air. The oxygen source for these microorganisms can be the organic material itself or alternatively may be supplied by inorganic oxides from within the input material. When the oxygen source in an anaerobic system is derived from the organic material itself, then the intermediate end products are primarily alcohols, aldehydes, organic acids, and/or carbon dioxide. In the presence of specialized methanogens, the intermediates are converted to the final end products of methane, carbon dioxide, and hydrogen sulfide. In an anaerobic system with methanogens, the majority of the chemical energy contained within the starting material is released by methanogenic microbes as methane.

In most cases biomass is made up of large organic molecules. In order for the microbes in anaerobic digestion systems to access the energy potential of the material, these chains must first be broken down into their smaller constituent parts. These constituent parts or monomers such as sugars are readily available to other microbes. The process of breaking these chains and dissolving the smaller molecules into solution is called hydrolysis. Hydrolysis of these high molecular weight polymeric components is a first step in anaerobic digestion. Through hydrolysis the complex organic molecules are broken down into simple sugars, amino acids, and fatty acids. Hydrogen produced in the first stages can be used directly by methanogens.

The biological process of acidogenesis is where there is further breakdown of the remaining components by acidogenic (fermentative) microbes. In acidogenesis, VFAs are created along with ammonia, carbon dioxide and hydrogen sulfide as well as other products.

A third stage of anaerobic digestion is acetogenesis. During acetogenesis simple molecules created through the acidogenesis phase are further digested by acetogens to produce acetic acid as well as carbon dioxide and hydrogen.

A fourth stage of anaerobic digestion is the biological process of methanogenesis. Methanogens utilize the intermediate products of the preceding stages and convert them into methane, carbon dioxide and water along with other products such as ammonia. The remaining, non-digestable material which the microbes cannot feed upon, along with any dead bacterial remains constitutes the digestate or biomass that can be removed from a system of the invention.

In an aspect, a bioreactor is disclosed that comprises: a first plurality of bacteria, wherein the first plurality of bacteria comprises aquatic anaerobic bacteria; and a second plurality of bacteria, wherein the second plurality of bacteria comprises ruminant anaerobic bacteria. In some embodiments, the ruminant bacteria is micro-aerophillic. In some instances, ruminants include, but are not limited to, sheep, cattle, bison, goats, and antelope. In some instances, the aquatic bacteria can be isolated from deep and shallow oceanic anoxic sediments, fresh water anoxic sediments, and marsh and peat bog anoxic sediments. Ruminant bacteria can be anaerobic bacteria that primarily produce volatile fatty acids. In some cases, the aquatic bacteria are methanogenic bacteria.

In some instances, a bioreactor herein comprises at least two modules. In some instances, a first module comprises primarily ruminant bacteria and a second module comprises primarily aquatic bacteria. The bioreactor can be a continuous system or a batch system. If the system is continuous, the bioreactor or modules of the bioreactor can be re-inoculated with anaerobic bacteria from time to time. In some instances, the bioreactor is a cylindrical vessel that can hold the biomass for a certain time before being removed. In some instance, the bioreactor is not a plug flow reactor. In some instances, any module of the bioreactor is configured to receive solid cellulosic biomass.

FIG. 1 illustrates an exemplary embodiment of a system of the invention comprising a primary and a secondary fermentation tank. The primary fermentation can comprise microbes, for example ruminant microbial species or other species capable of anaerobic digestion. Examples of microbial species that can be present in a tank of a system include, but are not limited to: *Fibrobacter succinogenes, Butyrivibrio fibrisolvens, Ruminococcus albus, Clostridium locheadii, Bacteroides ruminicola, Ruminobacter amylophilus, Selenomonas ruminantium, Succinomonas amylolytica, Streptococcus bovis, Selenomonas lactilytica, Megasphaera elsdenii, Schwartzia sunniovorans, Lachnospira mulitparus,* and *Neocalimastix*. Other ruminant microbial species can be present in a tank herein, as would be known to one skilled in the art.

In the primary fermentation tank in FIG. 1, the tank can receive cellulosic biomass and a microbial species. Populations of anaerobic microbes can take a period of time to establish themselves to be fully effective. Therefore in an embodiment, anaerobic microorganisms from materials with existing populations can be introduced. A tank can be pre-seeded or inoculated with the microbial species, or can be inserted at the same time or after the cellulosic biomass.

In some instances, aquatic anaerobic bacteria are present in volume:volume ratio of about 1:1 to ruminant anaerobic bacteria in the bioreactor system. In some instances, the first plurality of bacteria is present in a volume:volume ratio of about 1:1000 to the second plurality of bacteria in a first module of the system and the second plurality of bacteria is present in a volume:volume ratio of about 1:1000 to the first plurality of bacteria in a second module of the system. In some examples, the inoculation of aquatic anaerobic bacteria in a first module to ruminant bacteria is about 1:1, 1:2, 1:5, 1:10, 1:100, 1:500, 1:1000, or 1:10000 v/v. In an embodiment, the inoculation of aquatic anaerobic bacteria in a first module to ruminant bacteria is within the range of about 1:1 to 1:10000 v/v. In some instances, the inoculation of ruminant anaerobic bacteria in a second module to aquatic bacteria is about 1:1, 1:2, 1:5, 1:10, 1:100, 1:500, 1:1000, or 1:10000 v/v. In an embodiment, the inoculation of ruminant anaerobic bacteria in a second module to aquatic bacteria is within the range of about 1:1 to 1:10000 v/v. In some embodiments, the inoculation of the anaerobic bacteria in a module is completed using w/w ratios of ruminant and aquatic bacteria in ratios similar to the v/v ratios discussed herein.

In an embodiment, the biomass is removed from the primary tank about the time methanogenesis begins during the anaerobic digestion process. For example, the biomass can be removed shortly before methanogenesis, about the same time as methanogenesis occurs, or shortly after methanogenesis. In an embodiment, a methane sensor is used determine the amount of methanogenesis that is occurring in the primary tank. A user can determine to move the biomass out of the primary tank once a certain amount of methane is detected, in order to avoid too much methanogenesis in the primary tank.

In an embodiment, a process that occurs in the primary fermentation tank is cellulosic fermentation, for example, the conversion of cellulose to cellubiose to glucose to VFAs, or any combination of those steps. Another process that can occur in the primary tank is ammonification, for example, the conversion of amine groups of proteins to ammonia and ammonium. Also, desulfurylation of a protein containing sulfur atoms or of organic sulfur can occur in the primary fermentation tank, which generates hydrogen sulfide gas. As shown in FIG. 1, the primary fermentation tank generates a number of products including, but not limited to, biogases (such as hydrogen, carbon dioxide, hydrogen sulfide, and methane), water, VFAs (such as acetate, propionate, and butyrate), ammonia, and ammonium.

FIG. 1 also illustrates a secondary fermentation tank. The secondary fermentation tank is configured to receive biomass. The biomass can be from the primary fermentation tank. In the exemplary FIG. 1, the secondary tank receives biomass and anaerobic microbes that have completed the first three stages of anaerobic digestion. In an embodiment the secondary tank comprises methanogens that can be pre-seeded in the secondary tank or input with the biomass or input after the biomass. In an embodiment, the biomass also comprises microbes from the primary fermentation tank that can be broken down by methanogens in the secondary fermentation tank. Exemplary microbes that can be present in the secondary tank include, but are not limited to, *Methanobrevibacter ruminantium, Methanomicrobium mobile,* and *Syntrophomonas wolfei*. The secondary tank can also comprise other exemplary microbes including, but not limited to: syntrophic methanogens, *Methanobacterium formicum, Methanobacterium bryantii, Methanobacterium thermo-autotrophicum, Methanogenium cariaci, Methanogenium frigidum,* and *Methanothrix sochngenii*.

In an embodiment, a secondary fermentation tank produces biogases (such as methane, hydrogen sulfide, and carbon dioxide). In a further embodiment, the secondary tank can produce primarily methane. The processes of the secondary tank can include methanogenesis, for example the conversion of carbon dioxide in the presence of hydrogen to methane. Another process comprises ammonification wherein proteins of the biomass in the secondary tank are broken down into ammonia or ammonium. Desulfurylation can also occur in the secondary tank. Exemplary products from the secondary tank include without limitation: biogases (such as methane, hydrogen sulfide, and carbon dioxide), water, biomass slurry, ammonia, and ammonium.

In an embodiment, a system of the invention comprises a batch system. Biomass is added to the reactor at the start of the process in a batch and is sealed for the duration of the process. Biogas production may be formed with a normal distribution pattern over time. The operator can use this fact to determine when they believe the process of digestion of the organic matter has completed. A plurality of systems can be used in parallel to generate large quantities of products.

Another exemplary system comprises a continuous digestion processes wherein organic matter is added constantly or added in stages to the reactor. In a continuous system embodiment, the end products are constantly or periodically removed, resulting in constant production of biogas and other usable products. Examples of this form of anaerobic digestion include, but are not limited to, continuous stirred-tank reactors, upflow anaerobic sludge blanket, expanded granular sludge bed, and internal circulation reactors.

In an embodiment, a continuous digestion tank has a mechanical or hydraulic device, depending on the level of solids in the material, to mix the contents enabling the microbes and biomass to be in contact. A continuous system may also allow excess material to be continuously extracted to maintain a reasonably constant volume within the digestion tanks.

During continuous operation, the slurry level in the digestion system can remain relatively constant and the feed rate and effluent rate can be controlled to provide the desired overall residence time in the anaerobic digestion system. During continuous operation, feedstock can be continuously added to the reactor at approximately the same time that gas, effluent, scum, supernatant and/or sludge are removed from the reactor. During semi-continuous operation, feedstock can be added to the reactor incrementally and gas, effluent, scum, supernatant and/or sludge are removed incrementally at the same or different times. During batch operation, larger portions of feedstock are added to the reactor at given time intervals and larger portions of gas, sludge, effluent, supernatant and/or sludge are removed from the reactor at the same or different time intervals. During continuous operation, the operating temperature and rate of gas production will be relatively constant. In an embodiment, continuous operation provides a greater rate of gas production than batch or semi-continuous operation.

In an embodiment, the system comprises a single-stage digestion system is one in which all of the biological reactions occur within a single sealed reactor or holding tank. An exemplary one-stage reaction system is an anaerobic lagoon, for example, a pond-like earthen basin used for the treatment and long-term storage of waste.

The bioreactor can comprise an input for cellulose-containing feedstock and at least one output, wherein the output of the bioreactor consists of at least one of the following: ammonia, volatile fatty acids, and methane.

In an exemplary embodiment, the system comprises a two-stage or multi-stage digestion system with more than one digestion vessels in series. Acidogenic microbes produce organic acids such as VFAs and more quickly grow and reproduce than methanogenic microbes. Methanogenic microbes require stable pH and temperature in order to optimise their performance. In an embodiment of the system, hydrolysis, acetogenesis and acidogenesis occur within the first reaction vessel. A separator can be used after the first digestion vessel to extract products from the system and processes. For example, hydrogen and carbon dioxide gas, VFAs, water, and ammonia can be extracted after digestion in the first vessel and the remaining contents can be transferred to the second vessel as demonstrated in FIG. 1. In an embodiment, methanogenesis occurs in the second vessel, thereby primarily producing methane gas and a variety of other products including ammonia.

In an aspect, a bioreactor is disclosed that comprises: a first plurality of bacteria, wherein the first plurality of bacteria comprises bacteria in its acidogenic state; and a second plurality of bacteria, wherein the second plurality of bacteria comprises bacteria in its acetogenic state, wherein the removal of volatile fatty acids produced from the acetogenic bacteria present in the bioreactor at a ratio such to maintain the pH of the bioreactor between 5.9 and 8.4. In some instances, in a bioreactor without the removal of volatile fatty acids, the pH is not maintained between 5.9 and 8.4. In some instances, the first and second pluralities of bacteria both comprise aquatic anaerobic bacteria and ruminant anaerobic bacteria.

FIG. 2 demonstrates an exemplary system of the invention comprising two fermentation tanks, and at least to separators for obtaining products from the fermentation tanks. Biomass containing starches, proteins and cellulose materials can be input into the VFA chamber. Cellulosic biomass such as algae can be input into the VFA chamber through an input blender that breaks up the biomass. The feedstock can be input through a force-feed or gravity-feed system. Other exemplary systems of input for the feedstock include without limitation pumps of all types or gas pressurized feed tubes or chambers. Also, the input of the biomass can comprise an anoxic tank to remove oxygen from the biomass, in order for anaerobic digestion to proceed more readily. In an embodiment, a cellulose feedstock can be introduced into a pretreatment tank to condition or pretreat the feedstock to enhance anaerobic digestion prior to input in the VFA chamber. For example, one or more conditioning agents, such as recirculated digested effluent exiting the anaerobic treatment unit, enzymes, acids, alkalis, alkaline earths, nutrients, anaerobic seed solids, and surfactants, can be added to the biomass feedstock to enhance anaerobic decomposition. In another embodiment, the feedstock can be subject to heating before entering the system. Grit, such as dirt, sand, soil, stones, pebbles, rocks, feathers, hair and other such materials, can also be removed prior to addition of the feedstock slurry to the anaerobic digestion system. Exemplary equipment for removing grit includes, but is not limited to, classifiers, settling tanks, multiphase tanks, and filters.

The VFA chamber can comprise anaerobic microbes, such as those described herein. The VFA chamber can be seeded with microbes prior to the biomass input. In an example, a cow stomach is used to seed the VFA chamber with ruminant microbes that perform anaerobic digestion. Anaerboic digestion and fermentation occur in the VFA tank after input of the biomass and microbes. In some embodiments, mixing the feedstock in the tank can facilitate effective digestion. Mixing may be accomplished with conventional mechanical mixers or by circulating (bubbling) a gas or a portion of the captured biogas back into the tank. Exemplary mixers include, but are not limited to, one or more sparger bars, one or more mechanical agitators, a fluid recirculator, a gas recirculator and combinations thereof mechanical agitators which are useful in the anaerobic digestion system include all known fluid agitators such as a turbine, propeller, impeller, paddle, wheel, helical bar, stirrer, rotating reaction vessel, flexible tube or rod, magnetic agitator, tumbler, paddle wheel, and other mechanical agitators known to those of ordinary skill in the art of fluid mixing.

Within the tank, gas rises to the top of the tank and can be sampled or removed through an output located near the top of the VFA chamber. The output near the top can also comprise sensors in order to measure the different gas content of the chamber, which can be useful in determining the stage of anaerobic digestion within the tank. An output from the VFA chamber can transfer accumulated biogases from the VFA chamber to the BioGas chamber, for example carbon dioxide and hydrogen gas.

The VFA chamber can also comprise a pressure valve to regulate the pressure within the tank. A reaction vessel can be pressurized with a pressurizer. The pressurizer can be a compressed gas cylinder, pump, or other such equipment, that forces an inert gas, a produced gas, feedstock slurry, or reaction effluent into the reaction vessel to increase the pressure of the reaction vessel to the desired operating pressure. Accordingly, the feedstock slurry feeder, gas recirculator, fluid recirculator, sparger bar or combinations thereof can serve as the pressurizer. In an embodiment, the anaerobic digestion system comprises one or more pressure relief valves, vents or exhaust valves to reduce pressure within the reaction vessel. The anaerobic digestion system can also comprise a pressure controller capable of controlling pressure within the reaction vessel and/or a pressure monitor capable of monitoring pressure within the reaction vessel. The anaerobic digestion system can also comprise one or more pressure gauges that indicate the pressure within the system.

Biomass and liquid can occupy the tank below the gas layer. A sludge or solids layer can reside in the tank below the liquid layer. An output for removing the liquid from the VFA chamber can lead to a first separator. For example in FIG. 2, the first separator is a VFA vaporizer, wherein VFAs from the liquid are distilled and separated from the liquid. VFAs can also be collected using chromatography. Also, water can be removed from the liquid and from the system at the first separator, for example by distillation or drying. A heat exchanger may provide heat necessary for distillation and collection of the products from the liquid from the first chamber. VFAs typically gasify above about 120° C., while water boils at 100° C., and ammonia gasifies around −30° C. In an embodiment, the first separator comprises a plurality of separation devices. For example, the first separator can comprise distillation columns for the distillation of ammonia, water, and VFAs. In another embodiment, ammonia, water, and VFAs are removed by the same distillation column. In another embodiment, chromatography is used to remove and collect VFAs from a system or bioreactor herein. In some instances, the VFAs collected by the methods and systems herein are about 98.5% pure. The VFAs collected by the methods and systems herein can be about 85, 90, 95, 99, or 100% pure. In some instances, trace amounts of alcohols are collected with the VFAs.

Temperature affects the productivity of the anaerobic digestion system as different microbes have different optimal temperatures. The temperature of the reaction solution can be controlled with a temperature controller that heats and/or cools the reaction solution. The temperature controller can be a heater, heat exchanger, jacket surrounding the reaction vessel, coil within the reaction vessel or other such equipment used for controlling the temperature of fluids within reactors. The temperature of the reaction vessel can be monitored with a temperature monitor, such as a thermocouple or other equipment known to those of ordinary skill in the art. A heating or cooling jacket surrounding the reaction vessel is alternatively used to control the temperature of the reaction vessel contents. In an embodiment, the digestion system is maintained at ambient temperatures.

Fluid levels in the reaction vessel can be monitored with a fluid level detector and controlled with a fluid level controller that either increases or decreases the flow of feedstock slurry into or reaction effluent out of the reaction vessel.

In an embodiment, the VFA chamber is a mesophilic tank and maintained at a temperature of about 20-40° C. Further, the VFA chamber can be maintained at 25-32° C. Further yet, the VFA chamber can be maintained at ambient temperature. In an embodiment, the resident time of the biomass is 2-30 days in the VFA chamber. In another embodiment, the resident time to complete hydrolysis, acidogenesis, and acetogenesis of the biomass is 4-22 days. The resident time can be determined by a user, or can be automatically monitored by a computer system and sensors measuring the contents of the tank. In another embodiment, the quantity or concentrations of VFAs in the tank is monitored. In an example, the volume of a VFA chamber can be up to 1 million gallons. The VFA chamber can comprise about 5, 10, 15, or 20% solid material by weight. In an example, the VFA chamber comprise 10% solids by weight. In another embodiment, the VFA chamber is an 8 ton tank, of which about 10% of the 8 tons are solid, and the remaining 90% liquid and gas by weight. In another example of the system, the VFA tank is a 1 ton tank, of which about 10% of the 1 ton are solid and the remaining 90% liquid and gas by weight.

The residence time in a digestion system varies with the amount and type of feed material and the configuration of the digestion system. Methanogens, responsible for the final stage of anaerobic digestion, are only capable of doubling their population at a very slow rate of about 192 hours. Acetogenic microbes involved in the intermediate stage of anaerobic digestion have a doubling rate about 60 times faster than that of the methanogenic microbes.

As shown in FIG. 2, remaining liquid, biomass slurry, and sludge can be removed from the VFA chamber and input to the BioGas chamber. In an embodiment, the BioGas chamber comprises methanogens for the anaerobic digestion of the biomass slurry, liquid, and sludge into methane. Other microbes may be present in the BioGas chamber as well. In another embodiment, microbes are transferred from the VFA chamber to the BioGas chamber. For example, the microbes can now be a source of biomass for the BioGas chamber, or they may contribute to the digestion process in the second tank. Any leftover fatty acids or lipids form the membranes of the biomass or the microbes can be degraded as well. In an embodiment, the BioGas chamber also comprises an input for food waste or oils, or other greases, fats, or wastes, such as sewage sludge. In this manner, biomass, biomass waste, and other wastes containing proteins or cells can be converted to useful products by a process or system of the invention.

Biogases can be removed from the BioGas chamber from the top or near the top of the chamber. In an embodiment, more than 50, 60, 70, 80, or 90% of the biogas is methane. Other gases include carbon dioxide and hydrogen sulfide. Optionally, a gas separator can be used to fractionate the gas as required by a user. In an exemplary embodiment, such as the one in FIG. 2, a primary gas line from the BioGas chamber can comprise a sampler, sensor, and pressure valve which can be used to monitor and regulate the production biogas from the BioGas chamber. The content or percentage of each gas can be monitored using a gas chromatograph or other gas sensing or analyzing equipment used to determine the composition or presence of gases or gaseous mixtures.

In an embodiment, the BioGas chamber is a mesophilic tank and maintained at a temperature of about 20-40° C. Further, the BioGas chamber can be maintained at 25-32° C. Further yet, the VFA chamber can be maintained at ambient temperature. In another embodiment, the BioGas chamber is maintained at a thermophilic temperature (for example 55-80° C.), and comprises thermophilic methanogens. In an embodiment, the resident time of the biomass is 2-30 days in the BioGas chamber. In another embodiment, the resident time to complete methanogenesis of the biomass is 4-22 days. The resident time can be determined by a user, or can be automatically monitored by a computer system and sensors measuring the contents of the tank. In an embodiment, the rate of methane production is used to monitor the condition of the BioGas chamber. In an example, the volume of a BioGas chamber can be up to 1 million gallons. The BioGas chamber can comprise about 5, 10, 15, or 20% solid material by weight. In an example, the BioGas chamber comprises 10% solids by weight. In another embodiment, the BioGas chamber is an 8 ton tank, of which about 10% of the 8 tons are solid, and the remaining 90% liquid and gas by weight. In another example of the system, the WA tank is a 1 ton tank, of which about 10% of the 1 ton are solid and the remaining 90% liquid and gas by weight.

Also shown in FIG. 2, methane from the BioGas chamber can be used to power a turbine system that generates electricity and heat. For example, the heat from the turbine can be used with a heat exchanger of the system to separate or distill liquid products from the system.

In some embodiments, pH of the system can be monitored to determine the timing of collecting products from the system. For example, when the pH is higher or lower than a certain threshold, ammonia or VFAs can be removed from the system to maintain the pH around neutral. In some instances, the pH is about 5.9 to about 8.5. In an instance, the preferable pH of the system can be 6.9-7.3. In some instances, when the pH is less than 6.5, VFAs are collected from the systems. In some instances, when the pH is higher than 8.0, ammonia is collected from the system.

There are a number of parameters that can affect methane productivity of the microbes. Among these are the digestion system temperature; the stability of the digestion system temperature; intrusion of oxygen or air; fluctuations in pH; and build up of chemical products such as ammonia, hydrogen sulfide or excess volatile fatty acids.

In an aspect, a method of collecting products from cellulose-containing feedstock comprises: delivering the cellulose-containing feedstock to a bioreactor, wherein the bioreactor comprises a plurality of anaerobic bacteria; converting the cellulose-containing feedstock to usable products within the bioreactor, wherein the usable products include at least one of the following: ammonia, volatile fatty acids, and methane; and collecting the products from the bioreactor, wherein 59% or greater of the cellulose-containing feedstock by weight is converted to the products wherein the products are selected from the group consisting of volatile fatty acids, ammonia, and methane. In some instances, 60, 65, 70, 75, or 80% or greater of the cellulose-containing feedstock by weight is converted to the products. Examples of outputs that are not products for the purposes herein include non-digestable fibers such as lignin and other cellulosic fibers. In some instances, a feedstock delivered to a system or bioreactor herein comprises only small amounts of lignin or cellulosic fibers.

In some instances, the plurality of anaerobic bacteria comprise: a first plurality of bacteria, wherein the first plurality of bacteria comprises aquatic anaerobic bacteria; and a second plurality of bacteria, wherein the second plurality of bacteria comprises ruminant anaerobic bacteria. In some instances, the plurality of anaerobic bacteria comprise: a first plurality of bacteria, wherein the first plurality of bacteria comprises acidogenic bacteria; and a second plurality of bacteria, wherein the second plurality of bacteria comprises acetogenic bacteria, wherein the acidogenic bacteria and acetogenic bacteria are present in the bioreactor at a ratio such to maintain the pH of the bioreactor between 5.9-8.5.

In another aspect, a method is disclosed that comprises: combining a plurality of microorganisms from the deep-ocean with a plurality of microorganisms from a ruminant stomach in a vessel, wherein the pH in the vessel is maintained between 5.9-8.5, and wherein the pressure in the vessel is maintained between 0.5-10 atm.

Also shown in FIG. 2 is an output for removing the liquid products from the BioGas chamber. The output can be in communication with a second separator. In the example of FIG. 2, the second separator is capable of distilling ammonia and ammonium out of the liquid. The ammonia products can be stored and used in products such as fertilizer, for example without limitation ammonium sulfate, aqua ammonia, and ammonium phosphate. Ammonia can also be converted to other useful products like nitrates and nitrites. In another embodiment, the first separator can also remove ammonia or ammonium. Water can also be removed from the liquid at the second separator. FIG. 2 demonstrates the use of the water removed from the liquid to be recycled back into the VFA or BioGas chamber of a system of the invention to provide water to the microbes and biomass as they enter the tanks.

Figure 3:
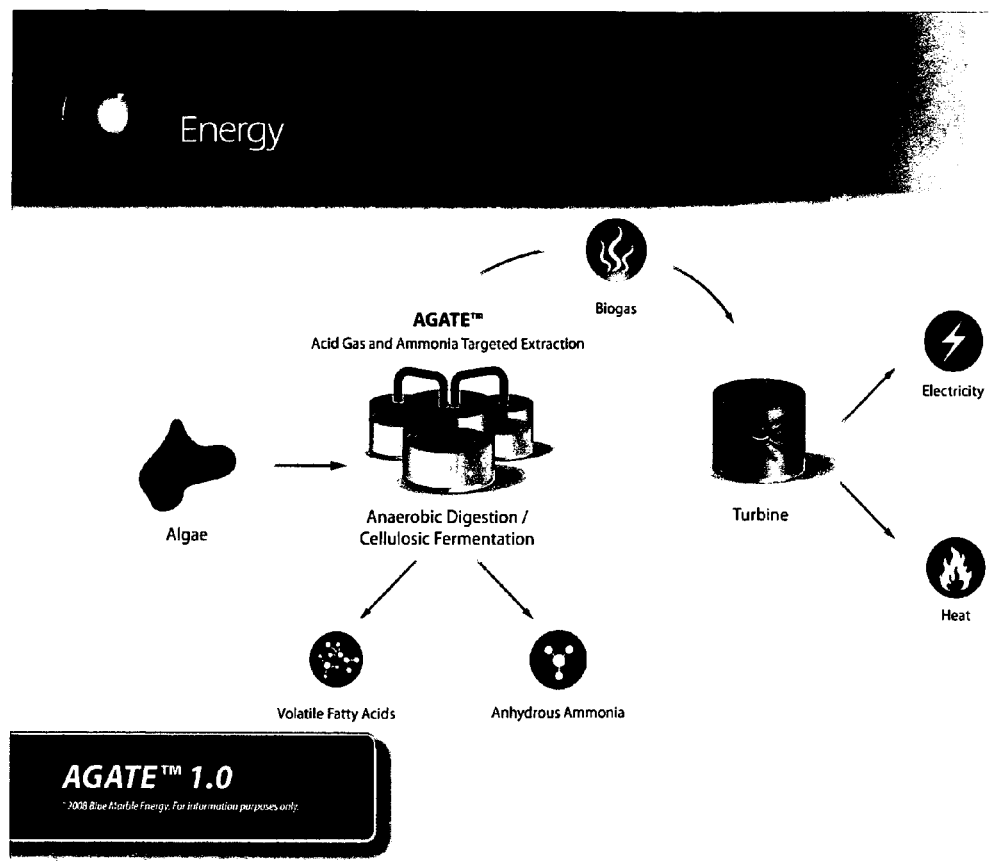
FIG. 3 demonstrates an exemplary system of the invention comprising a turbine and illustrates exemplary products.

FIG. 3 demonstrates an exemplary system of the invention comprising a turbine. A cellulosic biomass, such as algae, is entered into an anaerobic digestion, cellulosic fermentation system or apparatus (also referred to as AGATE or Acid Gas and Ammonia Targeted Extraction). The cellulosic biomass can be any biomass comprising cellulose and proteins. Examples of cellulosic biomass include, but are not limited to: algae, vascular plants, corn, soybean, palm, vegetable oil, waste vegetable oil, animal oil, animal fat, animal waste, manure, sewage, chicken tallow, beef tallow, and other described herein. In an embodiment, algae is the cellulosic biomass and is obtained from a photobioreactor. The photobioreactor can be a closed photobioreactor, a pond, or the sea. U.S. patent application Ser. No. 11/944,610 describes methods of collecting algal biomass for use in a system of the invention.

FIG. 3 also illustrates exemplary products obtained from an anaerobic digestion system. In the example, the anaerobic digestion system generates organic acids, anhydrous ammonia, and biogas. Biogas can comprise hydrogen gas, carbon dioxide, hydrogen sulfide, and methane. In an embodiment, the biogas can be used to drive a turbine, which in turn generates heat and electricity. The turbine can be a steam turbine based system adapted to use various fuels for producing the steam to rotate turbines. In various embodiments, steam production uses traditional fuels, such as coal and natural gas, as well as, alternative fuels, such as biogas, including methane. The steam is used to rotate turbines connected to an electric generator. The rotation of the generator produces electricity for distribution on a power grid. In other embodiments, the generating power plant uses a gas turbine generator and burns biogas, including methane, directly to generate electricity. In an embodiment, the heat generated from the turbine can be used to heat the anaerobic digestion system if necessary. In this embodiment the heat generated from the turbine is also used to extract anhydrous ammonia and volatile fatty acids. The turbine can also be driven by just the methane of the biogas. For example, the biogas collected from the anaerobic digestion system can be fractionated into its components. Methods of fractionating the biogas include, but are not limited to water scrubbing, pressure swing absorption, and size exclusion.

Anhydrous ammonia is also a product of the system of FIG. 3. Anhydrous ammonia can be useful for a variety of products including without limitation fertilizer. For example, anhydrous ammonia can be used for growing maize. Another product of the system of FIG. 3 is organic acids. The organic acids may comprise fatty acids and/or VFAs. VFAs are fatty acids with a carbon chain of six carbons or fewer, such as acetate, propionate, and butyrate. VFAs are naturally excreted during the cellulostic digestion process by the microbes in the tank, and in a ruminant ecology, absorbed by the stomach lining of the rumen. VFAs and VFA esters can be used in paints, solvents, industrial processing, fuel and foods for examples. In another embodiment, VFAs can be used as an organic solvent, for example, replacing toluene.

Figure 4:
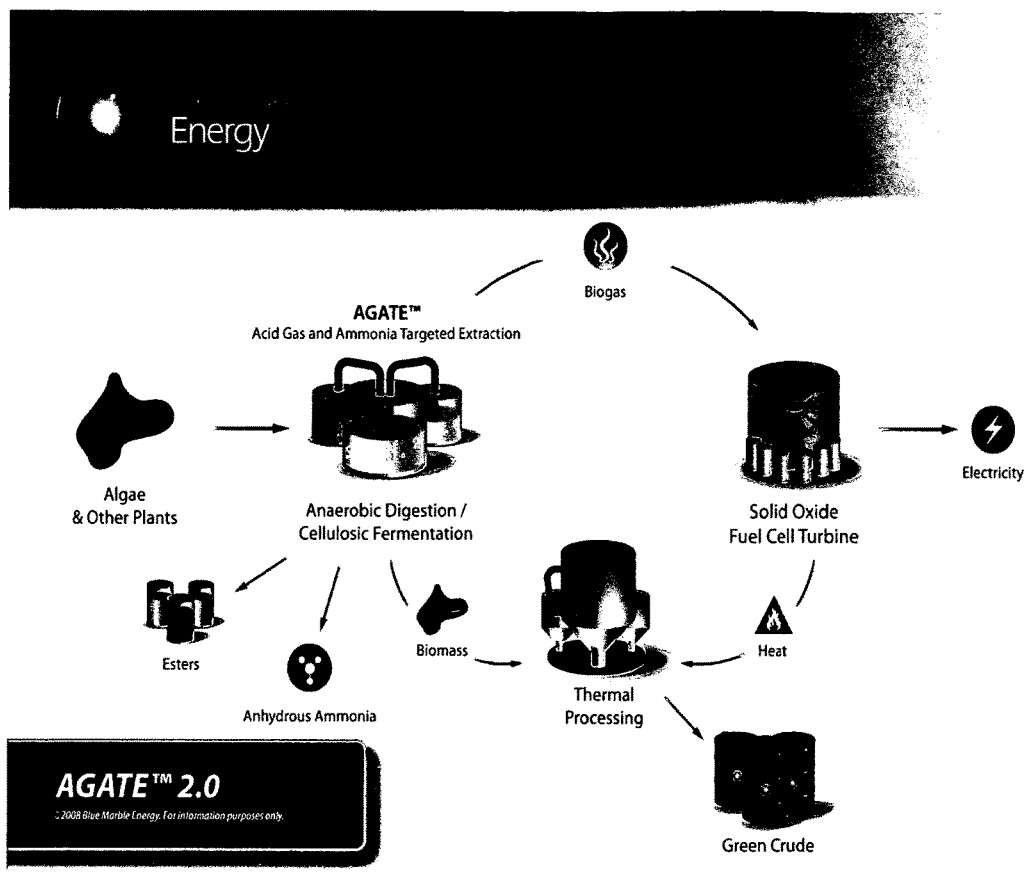
FIG. 4 illustrates an exemplary system of the invention comprising an anaerobic digestion system, a turbine, and a thermal processing unit.

FIG. 4 illustrates an exemplary system of the invention comprising an anaerobic digestion system, a turbine, and a thermal processing unit. In FIG. 4, cellulosic biomass enters an anaerobic digestion system of the invention. For example, algae and other plants can be input into the system. From the digestion system, numerous products can be obtained including, but not limited to, biogas, biomass sludge, anhydrous ammonia, and VFAs. In an embodiment as shown in FIG. 4, VFAs and other fatty acids from the system can be converted to esters and fatty acid esters. Fatty acid esters are useful in the creation of biodiesel and other fuel, as well as uses in the cosmetic and fragrance industries. In an embodiment, a system can produce biodiesel fuel. In general, a biodiesel fuel is a mixture of alkyl esters with combustion and energy content properties similar to petroleum based diesel fuel. Biodiesel is generated by transesterification of fatty acids and fatty acid esters of the biomass using simple alcohol. When VFAs are converted to esters, they may be added to conventional fuels to reduce the cloud point.

Another product of the exemplary system of FIG. 4 is anhydrous ammonia that has various indications in industries including without limitation: fertilizers, cleaning products, pharmaceuticals, foodstuffs, refrigeration, emission scrubbers, and laboratory uses. Biogas can also be obtained from the system of FIG. 4. The biogas from the system can include methane, carbon dioxide, hydrogen sulfide, and other gases. As shown in FIG. 4, methane can be used as fuel to operate a turbine, which in turn can generate heat and electricity for a wide array of uses.

The methane, carbon dioxide, or hydrogen produced by the anaerobic digestion system can be cleaned or purified by a scrubber to remove moisture, vapor, droplets, suspended solids or other such contaminants. The scrubber can comprise one or more of a filter, desiccant, zeolite, activated carbon, fiber, countercurrent wash solution, mixer, homogenizer, or other such components typically used in association with or comprised within gas scrubbers. Such components are well known to those of ordinary skill in the art of gas processing. The gases that exit the anaerobic digestion system or the scrubber are then optionally separated into their individual components using conventional gas separation equipment, which is known to those of ordinary skill in the art for separating gas mixtures. The gases may also be processed with one or more compressor, or dehydration equipment. Alternatively, the gases are stored in pressurized storage vessels or tanks after they have been scrubbed. If the stored gas is purified methane or hydrogen or mixtures of methane or hydrogen with carbon dioxide, it can be used directly to operate the anaerobic digestion system or one or more of its components or it can be used to operate additional equipment such as that described above. Ammonia may also be found in the above-described gases.

In the example in FIG. 4, heat and energy generated from the turbine can be routed to a thermal processing unit to perform a variety of tasks requiring elevated temperatures. The thermal processing unit can utilize heat of temperatures of greater than 300, 400, 500, 600, 700, or 800° C. An exemplary task as illustrated in FIG. 4, is refining of a oil, for example, refining of an oil from a biomass to generate green crude. The waste heat could be used in the thermal cracking or hydrocracking of an oil substance. In another embodiment, refining can be performed on a petroleum product to generate a fuel product such as gasoline or jet fuel.

Digestate is the solid remnants of the original input material to the digestion systems that the microbes cannot degrade. It also consists of the mineralized remains of the dead microbes from within the digestion systems. Digestate can come in three forms; fibrous, liquor or a sludge-based combination of the two fractions. In an exemplary two-stage system of the invention, the different forms of digestate come from different digestion tanks. Acidogenic digestate is a stable organic material comprised largely of lignin and cellulose, but also of a variety of mineral components in a matrix of dead bacterial cells and some plastic may be present. The material resembles domestic compost and can be used as compost or to make low grade building products such as fiberboard. A methanogenic digestate that is rich in nutrients and can be used as a fertilizer dependent on the quality of the material being digested. Digestate typically contains elements such as lignin that cannot be broken down by the anaerobic microorganisms. A maturation or composting stage may be employed after digestion. Large composting stages are typically used with dry anaerobic digestion technologies.

Biomass or biomass sludge from the digestion system is another product with a variety of uses that can be easily obtained from a system of the invention. The digested or partially digested biomass can be used in a variety of ways including without limitation a feedstock for generating animal or plant feed or for generating an oil or lipid product from the biomass. In an embodiment, a system comprises a processing unit that can be configured to, for example, dewater, dry, pelletize, and/or granulate the final processed biomass. Drying and/or granulating the solids can covert waste biomass into a usable fertilizer product or fertilizer ingredient and/or soil amendment product. The water removed from the solids fraction can be returned to the anaerobic digestion system. In addition, biomass solids produced by the system can contain significant levels of nitrogen, phosphorus, and other trace metals, and elements for creating a crop fertilizer and/or soil amendment.

In the example of FIG. 4, the biomass can be converted to an oil product such as green crude using the heat generated from a turbine running on biogas from the digestion system from which the biomass was removed. In another embodiment with a plurality of digestion systems, the biogas and biomass can be obtained from the same or different systems.

Figure 5:
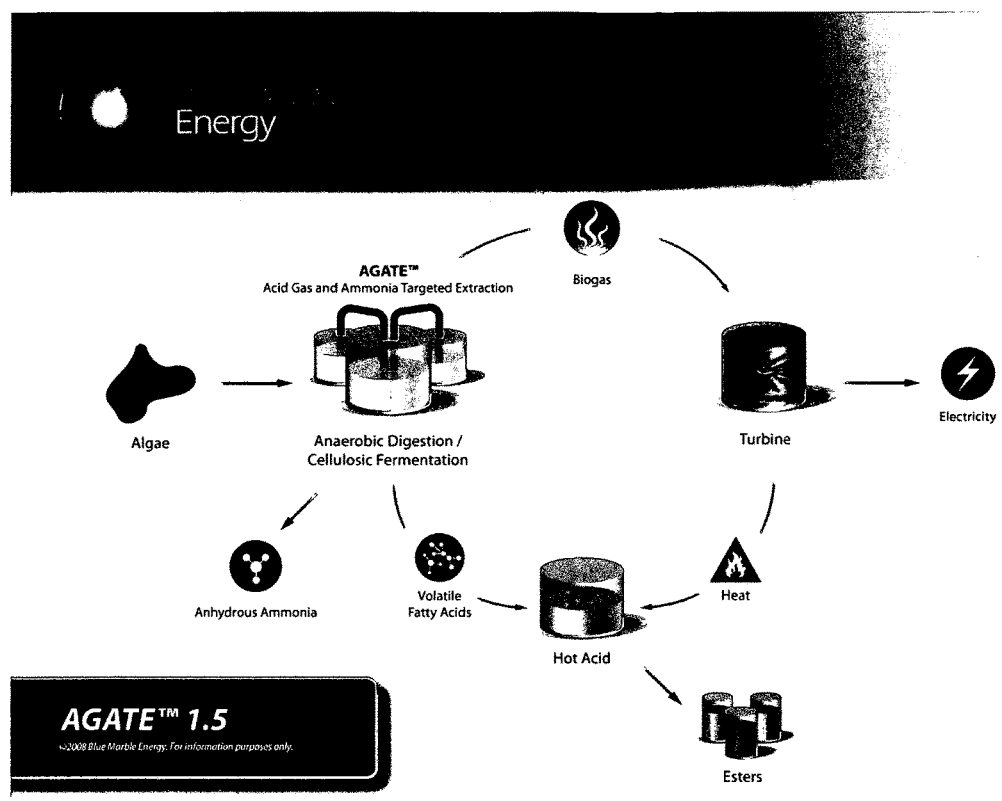
FIG. 5 illustrates an exemplary system of the invention comprising an anaerobic digestion system, a turbine to generate heat that can convert volatile fatty acids to hot acids and esters.

In an exemplary system as demonstrated in FIG. 5, volatile fatty acids can be heated to hot acids using heat generated by a turbine which can burn the biogas from the digestion system. The hot acid can be used for a variety of purposes including generating esters. The esters can be used for a number of products including biodiesel and biofuel.

Example 1

A bioreactor system as described herein was seeded with anaerobic bacteria, in particular aquatic and ruminant bacteria. The system was provided a number of different feedstocks. The feedstocks were provided 1 kg dry mass samples into a two tank bioreactor system as described herein. The first tank was seeded with 10 g of ruminant bacteria (in this example, bacteria from cattle) and 1 g of aquatic bacteria (obtained from mixed sediment), at a ratio of 10:1 w/w ruminant to aquatic anaerobic bacteria. In the second tank of the system, the seeding was reversed, or 10 g aquatic bacteria to 1 g of ruminant bacteria. FIG. 6 illustrates the conversion of the particular feedstocks in this exemplary system into selected products (listed across the top row of the table). The amount of product is displayed in grams, and the total weight of the products illustrates the quantity of the feedstock that was converted into a useful product (not including cellulosic fibers, etc). As demonstrated by the data, at least 59.8% of the feedstock was converted into a useful product across all the feedstocks. In addition, VFAs and biogases were produced in high quantities.

Example 2

*Ulva lactuca* harvested from the Puget Sound in two stage bioreactors was used as a feedstock on a bench scale. The bioreactors were inoculated with 10 mL of first chamber ruminant bacteria consortium consisting of over $10^9$ anaerobic colony forming units and an 0.01 mL of innoculum of anaerobic methanogenic sediment from a local peat bog that consisting of average of $10^8$ colony forming units along with 1 kg of dry biomass weight. The second reactor was inoculated with 10 mL of anaerobic methanogenic sediment and 0.01 mL of ruminant consortium. The *Ulva lactuca* feedstock in the bioreactor system produced the average equivalent of 220 cubic meters of biogas and provided average of 6 grams per liter of reactor of volatile fatty acids.

Example 3

Mixed macroalgal cultures were placed in a bioreactor system with the same innoculum as in Example 2. The feedstock was converted to an average equivalent of 580 cubic meters of biogas and average of 9.4 grams per liter of reactor of volatile fatty acids.

Example 4

Yard waste and grass clippings were placed in a bioreactor system with the same innoculum as in Example 2. The feedstock was converted to an average of 600 cubic meters of biogas and 16 grams per liter of volatile fatty acids from the samples.

Example 5

A two stage bioreactor system as described herein was utilized with a mixture of ruminant organisms, the mixture comprised equal parts bovine, goat, and sheep ruminant microbes in the 10 mL inoculation. Grass clippings and pulp mill waste were used as the feedstock. As compared to the other examples herein, the products from yielded from converting the feedstock showed decreased biogas yields (200-300 cubic meters) and increased volatile fatty acid production, showing an average production of 10.6 grams per liter of reactor of VFA production. The following microbes have been identified in the first module of Examples 2-5: *Lactobacillus, Clostridium propionicum, Clostridium butyricum, Enterobacter, Ruminococcus albus*. The following microbes have been identified in the first module of Examples 2-5: *Methanobrevilbacter ruminantium; Megasphaera elsdenii*

The other microbes described herein have been identified as present in a bioreactor system as described herein and in some of the systems of Examples 2-5.

What is claimed is:

1. A bioreactor system comprising:
   (a) a first module comprising a first plurality of anaerobic bacteria;
   (b) a second module comprising a second plurality of anaerobic bacteria;
   (c) an output of the first module connected to an input of the second module and configured to carry liquid, biomass, and sludge from the first module to the second module;
   (d) a first separator configured to remove volatile organic acids from the first module;
   (e) a second separator configured to remove ammonia from the second module; and
   (f) a monitor configured to activate the second separator in response to detecting a pH of the bioreactor system higher than 8.0, wherein the first plurality of anaerobic bacteria comprises a different mixture of anaerobic bacteria than the second plurality of anaerobic bacteria.

2. The bioreactor system of claim 1, wherein a majority of the first plurality of anaerobic bacteria is acidogenic bacteria, and wherein a majority of the second plurality of anaerobic bacteria is acetogenic bacteria.

3. The bioreactor system of claim 1, wherein a majority of the first plurality of anaerobic bacteria is acidogenic bacteria, and wherein a majority of the second plurality of anaerobic bacteria is methanogenic bacteria.

4. The bioreactor system of claim 1, wherein without the removal of volatile organic acids, the pH is not maintained between 5.9 and 8.0.

5. The bioreactor system of claim 1, wherein the first and second pluralities of anaerobic bacteria each comprise aquatic anaerobic bacteria and ruminant anaerobic bacterial.

6. The bioreactor system of claim 5, wherein a majority of the first plurality of anaerobic bacterial is ruminant anaerobic bacteria, and wherein a majority of the second plurality of anaerobic bacteria is aquatic anaerobic bacteria.

7. The bioreactor system of claim 5, wherein the first plurality of anaerobic comprises the ruminant anaerobic bacteria in a volume:volume ratio of about 100:1 to 1500:1 of the aquatic anaerobic bacteria, and wherein the second plurality of anaerobic bacteria comprises the aquatic anaerobic bacteria in a volume:volume ratio of about 100:1 to 1500:1 of the ruminant anaerobic bacteria.

8. The bioreactor system of claim 5, wherein the ruminant anaerobic bacteria is selected from a group consisting of the following: *Fibrobacter succinogenes, Butyrivibrio fibrisolvens, Ruminococcus albus, Clostridium locheadii, Bacteroides ruminicola, Ruminobacter amylophilus, Selenomonas ruminatium, Succinomonas amylolytica, Streptococcus bovis, Selenomonas lactilytica, Megasphaera elsdenii, Lachnospira multiparus, Neocalamastix*, and a combination thereof.

9. The bioreactor system of claim 5, wherein the aquatic anaerobic bacteria is selected from the group consisting of the following: *Methanobrevibacter ruminantium, Methanomicrobium mobile, Syntrophomonas wolfei*, and a combination thereof.

10. The bioreactor system of claim 1, wherein the first module comprises an input configured to receive a feedstock.

11. The bioreactor system of claim 1, wherein the first module comprises an output configured to collect volatile organic acids from the bioreactor system.

12. The bioreactor system of claim 1, wherein the second module comprises an output configured to collect ammonia from the bioreactor system.

13. The bioreactor system of claim 1, wherein the second module comprises an output configured to collect methane from the bioreactor system.

14. The bioreactor system of claim 1, wherein the second separator is a distillation separator or a vaporizer.

15. A bioreactor system for converting cellulose-containing feedstock into products, wherein the system comprises:
  (a) a first module comprising a feedstock input configured to receive a cellulose-containing feedstock, a first output and a second output, a first plurality of anaerobic microbes, and the cellulose-containing feedstock wherein the first plurality of anaerobic microbes digest the cellulose-containing feedstock to generate an organic acid product and a partially-digested feedstock;
  (b) a first separator in communication with the first output of the first module, the first separator configured to remove the organic acid product from the partially-digested feedstock;
  (c) a second module comprising a partially-digested feedstock input in communication with the second output of the first module, more than one output, and a second plurality of anaerobic microbes, wherein the partially-digested feedstock input receives a slurry of the partially-digested feedstock from the second output of the first module, and wherein the second plurality of anaerobic microbes digest the partially-digested feedstock to generate a methane product and an ammonia product; and
  (d) a second separator in communication with the second module, wherein the second separator is configured to remove the ammonia product from the partially-digested feedstock and wherein the first plurality of anaerobic microbes comprises a different mixture of anaerobic microbes than the second plurality of anaerobic microbes.

16. The bioreactor system of claim 15, wherein the first plurality of anaerobic microbes comprises ruminant anaerobic bacteria.

17. The bioreactor system of claim 15, wherein the second plurality of anaerobic microbes comprises aquatic anaerobic bacteria.

18. The bioreactor system of claim 15, wherein the first plurality of anaerobic microbes comprises a volume:volume ratio of about 100:1 to 1500:1 between ruminant anaerobic bacteria and aquatic anaerobic bacteria, and wherein the second plurality of anaerobic microbes comprises a volume:volume ratio of about 100:1 to 1500:1 between aquatic anaerobic bacteria and ruminant anaerobic bacteria.

19. A method of collecting products from cellulose-containing feedstock using the bioreactor system of claim 1, the method comprising:
  delivering a cellulose-containing feedstock to the first module of the bioreactor system;
  transferring partially-digested cellulose-containing feedstock and at least a portion of the first plurality of anaerobic bacteria to the second module of the bioreactor system;
  converting the cellulose-containing feedstock to usable products within the bioreactor system, wherein the usable products include the ammonia, volatile fatty acids, and methane; and
  collecting at least one of the volatile fatty acids from the first module or the ammonia and methane from the second module.

20. The method of claim 19, wherein the first plurality of anaerobic bacteria comprises ruminant anaerobic bacteria and the second plurality of anaerobic bacteria comprises aquatic anaerobic bacteria.

21. The method of claim 19, wherein the first plurality of anaerobic bacteria comprises acidogenic bacteria and the second plurality of anaerobic bacteria comprises acetogenic bacteria, wherein the acidogenic bacteria and acetogenic bacteria are present in the bioreactor system at a ratio such to maintain the pH of the bioreactor system between 5.9 and 8.0.

22. The method of claim 19, wherein 59% or greater of the cellulose-containing feedstock is converted to the usable products.

23. The method of claim 19, further comprising collecting volatile fatty acids in response to the pH of the bioreactor system dropping below a threshold level.

24. The method of claim 19, further comprising collecting ammonia in response to the pH of the bioreactor system increasing above a threshold level.

25. A method of converting biomass feedstock into products using the bioreactor system of claim 16, the method comprising:
  anaerobically digesting or breaking down the cellulose-containing feedstock in the first module to produce the organic acid product and the partially-digested feedstock;

separating the organic acid product from the partially-digested feedstock;

transferring the partially-digested feedstock to the second module;

anaerobically digesting or breaking down the partially-digested feedstock in the second module to produce the ammonia product and the methane product; and removing the ammonia product and the methane product from the second module.

* * * * *